United States Patent
Franklin et al.

(10) Patent No.: US 6,248,312 B1
(45) Date of Patent: Jun. 19, 2001

(54) COSMETIC COMPOSITIONS

(75) Inventors: Kevin Ronald Franklin; Adam Jan Kowalski, both of Bebington (GB); David Terence Parrott, Chicago, IL (US); Kathryn Elizabeth Rowe; Michael Stephen White, both of Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/548,310

(22) Filed: Apr. 12, 2000

(30) Foreign Application Priority Data

Apr. 12, 1999 (GB) .................................................. 9908202

(51) Int. Cl.[7] .............................. A61K 7/32; A61K 7/34; A61K 7/38; A61K 7/00
(52) U.S. Cl. ................................ 424/65; 424/66; 424/68; 424/400; 424/401
(58) Field of Search .................... 424/65, 66, 68, 424/400, 401

(56) References Cited

U.S. PATENT DOCUMENTS

| | | |
|---|---|---|
| 3,969,087 | 7/1976 | Saito et al. . |
| 4,673,570 | 6/1987 | Soldati . |
| 4,725,430 | 2/1988 | Schamper et al. . |
| 4,725,432 | 2/1988 | May . |
| 4,822,602 | 4/1989 | Sabatelli . |
| 4,948,578 | 8/1990 | Burger et al. . |
| 4,954,333 | 9/1990 | Ward . |
| 5,169,626 | 12/1992 | Tanner et al. . |
| 5,429,816 | 7/1995 | Hofrichter et al. . |
| 5,486,566 | 1/1996 | Katsoulis . |
| 5,587,153 | 12/1996 | Angelone, Jr. et al. . |
| 5,744,130 | 4/1998 | Guskey et al. . |
| 5,849,276 | 12/1998 | Guskey et al. ........................ 424/65 |

FOREIGN PATENT DOCUMENTS

| | | |
|---|---|---|
| 0 400 910 | 11/1995 | (EP) . |
| 0 512 770 | 10/1996 | (EP) . |
| 60-076543 | 5/1985 | (JP) . |
| 9-175977 | 7/1997 | (JP) . |
| 92/19222 | 11/1992 | (WO) . |
| 93/23008 | 11/1993 | (WO) . |
| 97/11678 | 4/1997 | (WO) . |
| 98/34588 | 8/1998 | (WO) . |

OTHER PUBLICATIONS

International Search Report Application No. PCT/GB 00/01228 (received in Unilever Patent Dept. Dec. 19, 2000).

Terech et al. "Low Molecular Mass Gelators of Organic Liquids and the Properties of Their Gels" Chem. Rev., vol. 97, 1997, pp. 3133–3159, —XP 002127859.

Ide et al. "Gelation of Fully Acylated Cellobiose in Alkane Solution" Bull. Chem. Soc. Japan, vol. 68, 1995, pp. 3423–3428—XP 002127501.

Takada et al. "Discotic Colunmar Liquid Crystals in Oligosaccharide Derivatives III. Anomeric Effects on the Thermo–Mesomorphic Properties of Cellobiose Octa–Alkanoates" Liquid Crystals, vol. 19, No. 4, 1995, pp. 441–448—XP 000545756.

*Primary Examiner*—Shelley A. Dodson
(74) *Attorney, Agent, or Firm*—Matthew Boxer

(57) ABSTRACT

A cosmetic composition preferably an antiperspirant composition, in solid or soft-solid form has a continuous phase which contains a water-immiscible liquid carrier and also contains a structurant which is partially or fully esterified cellobiose of the formula

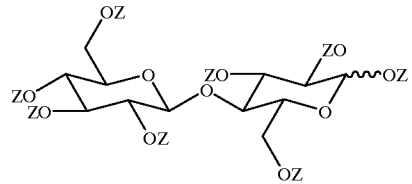

wherein each Z is independently hydrogen or an acyl group of the formula

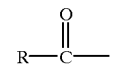

where R denotes a hydrocarbyl group containing from 4 to 22 carbon atoms. Not more than half of the Z groups are hydrogen.

34 Claims, No Drawings

COSMETIC COMPOSITIONS

FIELD OF THE INVENTION

The present invention relates to cosmetic compositions for application to human skin. Significant forms of the invention are concerned with antiperspirant compositions for application to human skin, especially the axilla. However, the invention can also be applied to other forms of cosmetic composition.

BACKGROUND OF THE INVENTION AND SUMMARY OF PRIOR ART

A wide variety of cosmetic compositions for application to human skin make use of a thickened or structured liquid carrier to deliver colour or some other active material to the surface of the skin. A significant example of such cosmetic compositions are antiperspirant compositions which are widely used in order to enable their users to avoid or minimise wet patches on their skin, especially in axillary regions.

Antiperspirant formulations have been provided with a range of different product forms. One of these is a so-called "stick" which is usually a bar of an apparently firm solid material held within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact.

Another possibility is that a stick is a softer solid composition accommodated in a dispensing container which in use extrudes the composition through one or more apertures.

Antiperspirant sticks can be divided into three categories. Suspension sticks contain a particulate antiperspirant active material suspended in a structured carrier liquid phase. Emulsion sticks normally have a hydrophilic phase containing the antiperspirant active in solution, this phase forming an emulsion with a second, more hydrophobic, liquid phase. The continuous phase of the emulsion is structured. Solution sticks typically have the antiperspirant active dissolved in a structured liquid phase which may be a mixture of water and a water-miscible organic solvent. This classification into suspension, emulsion and solution types can be applied to both firm and soft solid compositions.

Other types of cosmetic composition can also be provided in the form of a stick and again the stick may be a structured solution, emulsion or suspension. Examples of cosmetic compositions which are, or can be, marketed in a stick form are lipsticks, lip salves and eyebrow pencils.

There is substantial literature on the structuring or thickening of cosmetic compositions.

Conventionally, many sticks have been structured using naturally-occurring or synthetic waxy materials. Examples of these include those fatty alcohols which are solid at room temperature, such as stearyl alcohol, and hydrocarbon waxes or silicone waxes. Such materials are widely available, and by suitable selection of the materials themselves and their concentrations in the formulation, it is possible to obtain either a soft solid or a firm solid. Examples of these sticks are described in an article in Cosmetics and Toiletries, 1990, Vol 105, P75–78 and in U.S. Pat. Nos. 5,169,626 and 4,725,432. However, fatty alcohol or wax structured sticks tend to leave visible white deposits on application to human skin, and the deposits can also transfer onto clothing when it comes into contact with the skin and the wearer can, for example, find white marks at the armhole of the sleeveless garment.

Some alternative structurants have been proposed. The term "gellant" is often employed instead of "structurant". Where the resulting product is liquid of increased viscosity rather than a solid or gel, the term "thickener" can also be used. For example, the use of dibenzylidene sorbitol (DBS) or derivatives thereof has been proposed as gellant in a number of publications such as EP-A-512770, WO 92/19222, U.S. Pat. Nos. 4,954,333, 4,822,602 and 4,725,430. Formulations containing such gellants can suffer from a number of disadvantages, including instability in the presence of acidic antiperspirants, and comparatively high processing temperatures needed in the production of sticks.

A combination of an N-acylaminoacid amide and 12-hydroxy stearic acid to gel a non-aqueous formulation is described in, for example, WO 93/23008 and U.S. Pat. No. 5,429,816. However, high processing temperatures are needed to dissolve the gellants and prevent premature gelling. When applied to skin the formulation can be difficult to wash off, but reformulation to overcome that problem can be made impossible by the need for a high processing temperature.

The use of 12-hydroxy stearic acid without N-acylamino acid amide as a secondary gellant has been disclosed in some documents such as Japanese application 05/228915 and U.S. Pat. No. 5,744,130.

In WO 97/11678 to Helene Curtis, Inc, there is described the use of lanosterol as a gellant to make soft gels, sometimes in conjunction with a starch hydrolyzate derivative for antiperspirant compositions. This document includes a brief reference to cellulose as a possible ingredient. Cellulose is of course a polymer.

In WO 98/34588 to Lancaster Group GmbH, there is described the use of lanosterol as a gellant for oil-based cosmetic compositions, containing a cosmetic active material, of which one listed material is a deodorant, though not exemplified.

EP-A-400910 discloses cosmetic compositions in which a powdered form of cellulose is used as an absorbent for liquid material. In one example such a powder is used to absorb volatile silicone and the resulting material is used as a particulate ingredient in a stick which also contains particulate antiperspirant active and a binder polymer.

Antiperspirant emulsion sticks without any material identified as a structurant have been disclosed in U.S. Pat. Nos. 4,673,570, 4,948,578 and 5,587,153.

Cosmetic compositions other than antiperspirants which take the form of structured liquids have been disclosed, for example in U.S. Pat. Nos. 3,969,087, which disclosed the use of N-acylamino acids and derivatives thereof as gelling agents, U.S. Pat. No. 5,486,566 which utilised 12-hydroxy stearic acid.

SUMMARY OF THE INVENTION

It is an object of the present invention to provide thickened or structured cosmetic compositions, especially but not exclusively antiperspirant compositions, in which a liquid carrier material is thickened or structured using a structuring agent which is different from those mentioned above. A further object of the invention is to provide a structurant which can have superior properties to at least some of the structurants which have been used previously.

A further object of at least some forms of the invention is to provide compositions which exhibit low visible deposits.

Certain particularly preferred forms of the invention have the objective of providing compositions which have a measure of clarity, i.e. are translucent or even transparent.

According to a first aspect of the present invention there is provided a composition of matter suitable for cosmetic use having a continuous phase which comprises water-immiscible liquid carrier and a structurant therein which is wholly esterified or partially esterified cellobiose in which at least half the available hydroxyl groups have been esterified to bear acyl groups containing at least four carbon atoms. Such a compound has the formula:

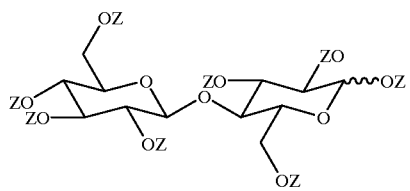

wherein each Z is independently hydrogen or an acyl group of the formula

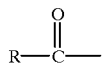

where R denotes a hydrocarbyl group containing from 4 to 22 carbon atoms, with the proviso that not more than half of the Z groups are hydrogen.

The fully or partially esterified cellobiose serves as a structuring agent or thickener for the water-immiscible liquid carrier and when used in a sufficient amount, which is likely to be less than 15% of the total composition, is able to structure this liquid into a gel with sufficient rigidity to sustain its own shape.

Without being bound to any specific theory or explanation, it is believed that the esterified cellobiose forms a network of fibres or strands extending throughout the liquid phase. Upon heating the gel to the gel melting temperature, the strands of structurant dissolve and the liquid phase becomes more mobile.

In order to promote good sensory properties at the time of use it is preferred to include silicone oil in the water-immiscible carrier liquid. The amount of silicone oil may be at least 10% by weight of the composition and/or at least 40% by weight of the water-immiscible carrier liquid.

Ethanol gives a cooling effect on application to skin, because it is very volatile. It is preferred that the content of ethanol or any monohydric alcohol with a vapour pressure above 1.3 kPa (10 mmHg) is not over 15% better not over 8% by weight of the composition.

As will be explained in more detail below, the structured water-immiscible carrier liquid may be the continuous phase of a composition with a dispersed second phase, either an emulsion or a suspension of particulate solid. Such a solid may be a particulate antiperspirant active. A disperse phase may be a solution of antiperspirant active in water or other hydrophilic solvent.

Certain preferred forms of this invention are concerned with compositions which are translucent or transparent. As is already known, translucent or transparent compositions can be obtained if it is possible to match the refractive indices of the different constituent phases present in the composition.

We have found that compositions within this invention which are a novel transparent or translucent emulsion can be obtained by formulating the composition to meet two criteria. Firstly the disperse phase and the continuous phase (consisting of the water-immiscible carrier liquid and the structurant contained within that liquid) should be formulated so that their refractive indices match. The refractive index of the continuous phase will be close to the refractive index of the water-immiscible carrier liquid in it. In order to achieve good light transmission through a composition, the refractive index of the water-immiscible continuous phase and the refractive index of the disperse phase should match within 0.003 units preferably 0.002 units.

Secondly, the matched refractive indices of these two phases should lie in a range which is an approximate match to the refractive index of the structurant. When the structurant is a cellobiose ester of $C_8$ or $C_9$, i.e. octanoic or nonanoic, acids a range from 1.40 to 1.50 preferably from 1.41 to 1.47 has been found suitable as will be explained below in greater detail.

One considerable advantage of preferred structurant materials of this invention is that they have a refractive index at a convenient value such that it is not difficult to formulate the rest of the composition to have a sufficiently close refractive index, and in addition the particularly preferred structurants are tolerant of mis-match between their refractive index and the matched refractive indices of the continuous and disperse phases.

Further advantages of preferred structurant materials of this invention are that they do not require high processing temperatures and that they are chemically stable, both during processing and in the resultant compositions. The avoidance of high processing temperatures can be especially valuable when the composition contains some water or other volatile constituent.

A composition of this invention will generally be marketed in a container by means of which it can be applied at time of use. This container may be of conventional type.

A second aspect of the invention therefore provides a cosmetic product comprising a dispensing container having at least one aperture for delivery of the contents of the container, means for urging the contents of the container to the said aperture or apertures, and a composition of the first aspect of the invention in the container.

The compositions of this invention can be produced by conventional processes for making suspension or emulsion solids or soft-solids.

Thus, according to a third aspect of the present invention there is provided a process for the production of a cosmetic composition comprising, not necessarily in any order, the steps of incorporating into a water-immiscible liquid carrier a structurant which is said wholly esterified or partially esterified cellobiose, if required, mixing the liquid carrier with a solid or a disperse liquid phase to be suspended therein, heating the liquid carrier or a mixture containing it to an elevated temperature at which the structurant is soluble in the water-immiscible liquid carrier, followed by introducing the mixture into a mould which preferably is a dispensing container, and then cooling or permitting the mixture to cool to a temperature at which it is thickened or solidified.

A suspended solid may be an antiperspirant active and a disperse phase may be a solution of such an active in a hydrophilic or polar solvent.

According to a fourth aspect of the present invention, there is provided a method for preventing or reducing perspiration on human skin comprising topically applying to the skin a composition comprising an antiperspirant active, a water-immiscible liquid carrier and a structurant therefor which is wholly esterified or partially esterified cellobiose.

DETAILED DESCRIPTION AND EMBODIMENTS

As mentioned above the invention requires fully esterified or partially esterified cellobiose as a structurant material for a water-immiscible liquid phase. Other materials may also be present depending on the nature of the composition. The various materials will now be discussed by turn and preferred features and possibilities will be indicated.

Esterified Cellobiose

The core structure of the structurant is cellobiose. This contains two glucose residues joined through a β-1,4 linkage. The cellobiose must be esterified on many, if not all of the available hydroxyl groups. It is convenient to utilise cellobiose which has been fully esterified but partially esterified cellobiose can be employed provided at least half of the hydroxyl groups have been esterified, better a higher proportion such as at least 5 or 6 out of every 8 hydroxyl groups.

The acyl groups should contain at least 4 carbon atoms. It is unlikely that they will contain more than 22 carbon atoms. It is preferred that the acyl groups are aliphatic with 6 to 18 or 19 carbon atoms and more particularly preferred that each acyl group incorporates an alkyl or alkenyl chain of 5 to 12 or 18 carbon atoms so that the acyl group contains 6 to 13 or 19 carbon atoms. Particularly preferred acyl groups incorporate a linear alkyl chain of 7 to 10 carbon atoms and are thus octanoyl, nonanoyl, decanoyl or undecanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where the mean acyl chain length m has a value in a range from 7 to 10 or 11. Commercially available feedstocks for these acyl groups are likely to include a small percentage of acyl groups which differ from the majority and may have a branched rather than linear chain. Thus it is likely that more than 90% but less than 100% of the acyl groups will meet the desired criterion of chain lengths in a range from m−1 to m+1 carbon atoms.

Linear aliphatic acyl groups may be obtained from natural sources, in which case the number of carbon atoms in the acyl group is likely to be an even number or may be derived synthetically from petroleum as the raw material in which case both odd and even numbered chain lengths are available.

Synthetic methods for the esterification of saccharides are well known. The esterification of cellobiose has been reported by Takada et al in *Liquid Crystals*, (1995) Volume 19, pages 441–448. This article gives a procedure for the production of the alpha anomers of cellobiose octa-alkanoates by esterification of β-cellobiose using an alkanoic acid together with trifluoracetic anhydride. The same article also reports the preparation of the beta anomers of cellobiose octa-alkanoates by a synthetic route utilising the appropriate acid chloride in the presence of pyridine. However, we have found that the alpha anomers are more effective structurants.

The amount of esterified cellobiose structurant in a composition of this invention is likely to be from 0.1 or 0.5 to 15% by weight of the whole composition and preferably from 0.5 up to 8% or 10%, probably from 1 to 8%. If the composition is an emulsion with a separate disperse phase, the amount of esterified cellobiose structurant is likely to be from 0.5 to 20% or even 25% by weight of the continuous phase, more likely from 1% to 15% of this phase.

Carrier Liquid

The water-immiscible carrier liquid comprise one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ $m^2$/sec (10 centistokes), and particularly above $10^{-7}$ $m^2$/sec (0.1 centistokes), the linear siloxanes normally exhibiting a viscosity of below $5 \times 10^{-6}$ $m^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0 to 100% by weight of one or more liquid silicones. Preferably, there is sufficient liquid silicone to provide at least 10%, better at least 15%, by weight of the whole composition. If silicone oil is used, volatile silicone preferably constitutes from 20 to 100% of the weight of the carrier liquid. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters, but these can be used as only part of the liquid carrier, desirably not above 20%, and possibly less than 10% by weight of the water-immiscible liquid carrier.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polyglycols such as PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Silicon-free liquids can constitute from 0–100% of the water-immiscible liquid carrier, but it is preferred that silicone oil is present and that the amount of silicon-free constituents preferably constitutes up to 50 or 60% and in many instances from 20 to 60% by weight of the carrier liquid.

Liquid Disperse Phase

If the composition is an emulsion in which the esterified cellobiose acts as a structurant in the continuous phase, the emulsion will contain a more polar disperse phase. The disperse phase may be a solution of an active ingredient.

The hydrophilic disperse phase in an emulsion normally comprises water as solvent and can comprise one or more water soluble or water miscible liquids in addition to or replacement for water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may also be advantageous. They can give good hardness even though the concentration of esterified cellobiose structurant may be only a small percentage of the total composition.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10–25, steareth-10–25 (i.e. $C_{16}$ to $C_{18}$ alcohols ethoxylated with 10 to 25 ethylene oxide residues) and PEG-15-25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPR™, Span™, Tween™, SF1228, DC3225C and Q2-5200.

Antiperspirant Actives

If the composition is an antiperspirant, it will contain an antiperspirant active. Antiperspirant actives, are preferably incorporated in an amount of from 0.5–60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n–nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a composition normally includes the weight of any water of hydration and any complexing agent that may also be present in the solid active. However, when the active salt is in solution, its weight excludes any water present.

If the composition is in the form of an emulsion the antiperspirant active will be dissolved in the disperse phase. In this case, the antiperspirant active will often provide from 3 to 60% by weight of the aqueous disperse phase, particularly from 10% or 20% up to 55% or 60% of that phase.

Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 $\mu$m with a mean particle size often from 3 to 20 $\mu$m. Both larger and smaller mean particle sizes can also be contemplated such as from 20 to 50 $\mu$m or 0.1 to 1 $\mu$m.

Optional Ingredients

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Irgasan DP300™ (Triclosan), Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a C8 to $C_{22}$ alkyl moiety and a hydrophilic moiety which can comprise a polyoxyalkylene group (POE or POP) and/or a polyol.

A further optional constituent of the formulation comprises one or more secondary structurants which can be employed in addition to the esterified cellobiose which is the primary structurant. The amount of such secondary structurants in the formulation is often zero, and usually not more than 15% of the formulation. It is normally not greater than the amount of the primary structurant.

The secondary structurants employable herein can be non-polymeric or polymeric. Solid linear fatty alcohol and/ or a wax may be included but are not preferred. Non-polymeric structurants, sometimes referred to as gellants, can be selected from fatty acids or salts thereof, such as stearic acid or sodium stearate or 12-hydroxy stearic acid. Other suitable gellants can comprise dibenzylidene alditols, e.g. dibenzylidene sorbitol. Further suitable gellants can comprise lanosterol, selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N'-dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Translucent/Transparent Compositions

If a composition of this invention is formulated as an emulsion it is possible to construct the formulation such that the emulsion is translucent or transparent. In order to do this the refractive indices of the water-immiscible continuous phase and the polar or aqueous disperse phase must be matched to each other and the value of refractive index at which they are matched must also approximately match the refractive index of the structurant.

The refractive index of a fibrous network of a structurant can be determined by using that structurant to gel a number of oils or oil mixtures of differing refractive index. When the resulting gel is transparent, the refractive index of the oil or oil mixture(which can be determined by conventional measurement) is a good approximation to the refractive index of the structurant. The oils or mixtures or oils should be chosen from these which are gelled well by the structurant to avoid interfering effects.

Using this method we have determined the refractive index of a preferred esterified cellobiose, namely cellobiose octa-nonanoate, to fall in a range between 1.45 and 1.50, being approximately 1.48 at 22° C.

When the structurants are cellobiose esters of $C_9$ or shorter fatty acids, we have found that the value at which the refractive indices of the continuous and disperse phases are matched can be somewhat below the refractive index of the structurant, down to a value of 1.42 or even down as far as 1.41 or 1.40. A value slightly above 1.48 would be useable also, but is inconvenient to achieve.

When the structurants are esters of $C_{10}$ or longer acids, the matched refractive indices of the two phases have to be closer to 1.48. For cellobiose octa-decanoate the refractive index of the two phases needs to be above 1.44 and preferably above 1.45 in order to obtain a high level of translucency.

For the continuous phase, silicon-free water-immiscible liquid oils generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C., but carrier liquid mixtures with refractive indices in the range from 1.41 to 1.46 can be obtained by mixing volatile silicone with other oils. Non-volatile silicone oils generally have refractive indices in a range from 1.45 to 1.48 at 22° C. and so can be included when desired.

The refractive index of the continuous phase will be very close to the refractive index of the carrier liquid (usually a carrier liquid mixture) which is its principal component.

For the disperse phase, a solution of an antiperspirant active salt in water alone will generally display a refractive index below 1.425. The refractive index can be raised by incorporating a diol or polyol into the aqueous solution. It is believed to be novel to match the refractive index of a polar disperse phase to that of a structurant network within a continuous phase. Moreover, it can be achieved without using so much diol or polyol as will make the composition excessively sticky.

If composition of this invention is a gelled continuous phase without any disperse phase, it can be made transparent or translucent by approximating the refractive index of the liquid carrier to that of the esterified cellobiose structurant in the manner discussed above.

For a composition which is a suspension the route to a transparent or translucent composition is to match the refractive indices of the liquid carrier and the suspended solid to that of the esterified cellobiose. Particulate antiperspirant actives which are anhydrous solids generally have a refractive index substantially above 1.50 which is brought down by hydration, but we have found that it is not easy to obtain an antiperspirant active with a refractive index of 1.48 or below even if the active is partially hydrated to lower its refractive index.

For this reason, a feature within this invention is to prefer the emulsion form of antiperspirant stick when seeking to achieve a transparent or translucent product.

For the regular production of compositions with optimum transparency it may prove desirable to monitor the refractive indices of the raw materials to detect any batch to batch variation. If necessary the composition of a liquid phase can be adjusted by variations in the quantity of a constituent material.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9° 10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Texture analyser

The hardness of a softer solid can be measured by using a texture analyser. This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument. After positioning the sample, the sphere position was adjusted until it was just above the sample surface. Texture Expert Exceed software was used to generate the subsequent motion profile used in the test method. This profile initially indented the sphere into the sample at an indentation speed of 0.05 mm/s until a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in stick barrels, which had a screw mechanism, or in 15 ml glass jars. For the barrel samples, the stick was wound up until it protruded above the edges of the barrel and then a knife was used to skim the top of the barrel in such a way as to leave a flat uniform surface. The stick was then pushed back into the barrel as far as possible to minimise any mechanical interference resulting from the compliance of the screw mechanism in the pack. Two indents were generally made either side of the screw. The samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{max}[N]}{A_p[mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop *Instron Universal Testing Machine* (Model 5566) fitted with a 10 N load cell, and the data analysis performed in the same way.

iii) Deposition and whiteness of deposit

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrates used were a: 12×28 cm strip of grey abrasive paper (3M™ P800 WetorDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

It has been found desirable to carry out deposition of a standard stick composition in the manner specified above, and determine the whiteness of the deposit, as a control.

iv) Light Transmission

The translucency of a composition may be measured by placing a sample of standardised thickness in the light path of a spectrophotometer and measuring transmittance, as a percentage of light transmitted in the absence of the gel.

We have carried out this test using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. We have observed that a composition which gives a transmittance of as little as 1% in this test is perceived by eye as "translucent". If a stick is made from a composition with 3% transmittance, it is possible to see cavities made by boring beneath the surface of the sample. By contrast, a conventional stick structure with stearyl alcohol is so opaque that it is impossible to see beneath its surface. A transmittance measured at any temperature in the range from 20–25° C. is usually adequately accurate, but measurement is made at 22° C. if more precision is required. In a number of preferred examples we have achieved a transmittance of 20% or above.

Preparation

Compositions of this invention can be produced by conventional processes for making suspension or emulsion solids or soft-solids. Such processes involve forming a heated mixture of the composition at a temperature which is sufficiently elevated that all the esterified cellobiose structurant dissolves, pouring that mixture into a mould, which may take the form of a dispensing container, and then cooling the mixture whereupon the structurant solidifies into a network of fibres extending through the water-immiscible liquid phase.

A convenient process sequence for a composition which is a suspension comprises first forming a solution of the esterified cellobiose structurant in the water-immiscible liquid. This is normally carried out by agitating the mixture at a temperature sufficiently high that all the structurant dissolves (the dissolution temperature) such as a temperature in a range from 50 to 120° C. Thereafter the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the esterified structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied in aqueous solution which can be utilised as is). This solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If necessary a pressurised apparatus could be used to allow a higher temperature to be reached, but with the structurant materials of this invention this is usually unnecessary. After two phases are mixed, the resulting mixture is filled into dispensing containers, typically at a temperature 5 to 30° C. above the setting temperature of the composition, and allowed to cool as described above for suspension sticks.

EXAMPLES

The examples below were prepared using a number of materials set out with their proprietary names in the following list. All temperature are in degrees Celsius. Refractive indices were measured at 22° C.
1 & 2) Volatile cyclic silicones (cyclomethicones) DC 245 and DC 345 (Dow Corning)
3 & 4) Non-volatile silicone fluids DC 556 and DC 710 (Dow Corning)
5) Polydecene (Silkflo 364NF from Albemarle)
6) Isostearyl Alcohol (abbreviated to ISA—Prisorine 3515 from Unichema)
7) C12–15 alkyl benzoate (Finsolv TN from Fintex)
8) Mineral Oil (Sirius M70 from Dalton)
9) Polypropyleneglycol 14 butylether (Fluid AP from Amercol)
10) Isopropyl myristate (abbreviated to IPM from Unichema)
11) Cetyl dimethicone copolyol (Abil EM90 emulsifier from Th. Goldschmidt)
12) Al/Zr Tetrachlorohydrex glycine complex (AZAG-7167 from Summit)
13) 50% aqueous solution of Al/Zr pentachlorohydrate (Zirkonal 50 from Giulini)
14) Superfino talc (particle size about 5 μ from Cyprus Minerals)
15) Glycerol (from Aldrich)
16) Propylene glycol (from Fisons)
17) Al/Zr Tetrachlorohydrex glycine complex 30% in propylene glycol (WA2Z 8106 from Westwood)
18) Al/Zr tetrachlorohydrex glycine complex (AZG-375 from Summit)
19) Isohexadecane (Permethyl 101A from Presperse Inc)
20) Isoeicosane (Permethyl 102A from Presperse Inc).
21) Bis-phenylpropyldimethicone, a non-volatile silicone fluid (SF 1555 from G E Silicones)
22) Polyglyceryl polyricinolate (Quest PGPR)
23) 1-octyldodecanol (Eutanol G from Henkel/Cognis)
24) Hydrogenated polyisobutene (Panalene-L-14E from Amoco)
25) Hydrogenated polyisobutene (Fancol 800 from Fanning Corp)
26) Polyglyceryl-3-diisostearate (Lameform TGI from Henkel/Cognis)
27) Polyglyceryl-2-dipolyhydroxystearate (Dehymuls PGPH from Henkel/Cognis)
28) Polyalpha olefins (Puresyn 4 from Mobil Chemical)
29) Ceteareth 20 (Eumulgin B2 from Henkel)
30) C20–C40 alcohols (Unilin 425 from Petrolite)

Example 1

Cellobiose was esterified with nonanoic acid to yield the fully esterified product in the form of its α-anomer following a procedure generally as described in Takada et al, Liquid Crystals, Volume 19, page 441 (1995).

The following materials were used:
β-D-cellobiose, 20 grams, 0.058 moles Nonanoic acid, 591.6 grams, 3.74 moles Trifluoroacetic anhydride, 297.6 grams, 1.42 moles.

These materials were obtained from Acros Organics—Fisher Scientific.

Into a 2 litre flange pot equipped with an overhead stirrer, water condenser and addition inlet was placed the nonanoic acid together with the trifluoroacetic anhydride. The resultant clear mixture was stirred up and heated to 100° C. using a silicone oil bath and temperature probe. During heating it was noted that the colour of the reaction mixture darkened and developed a dark brown tinge. After allowing the mixture to stir for one hour at 100° C., the cellobiose was slowly added via a solid powder funnel to the dark activated solution, and a dirty brown suspension was formed which re-dissolved forming a clear black solution within 10–20 minutes.

The reaction flask was then maintained at 100° C. for a total of 6 hours then cooled down to ambient laboratory temperature. Next the contents of the flask were transferred into 2 litres of methanol containing 10% de-ionised water in an ice-cooled 5 litre beaker. Immediately an off-white solid precipitate came out of solution, this was filtered off and collected. The crude solid was recrystallised a total of 4 times from a tetrahydrofuran/methanol solution producing a white solid product.

The product was obtained in a quantity of 31.5 g which was a 37% yield. It had a melting point of 110° C. The infra-red spectrum showed an absorption peak at 1739 cm$^{-1}$ for the ester carbonyl group. The amount of free acid could be determined from its absorption peak at 1705 cm$^{-1}$.

The n.m.r. spectrum showed the amount of cellobiose which was fully esterified and the proportions of product which were the α- and β-anomers.

The same procedure was followed using acids of different chain lengths. The acids used and details of the products are set out in the following table.

| | Properties of product | | | |
|---|---|---|---|---|
| Acid used | Mpt (° C.) | % of α-anomer | % fully esterified | Comments |
| Hexanoic | 104.9 | 95% | 86% | no free acid white solid |
| Heptanoic | 110 | 100% | 100% | white needles |
| Octanoic | 110 | 98% | 100% | no free acid white fluffy powder |
| Nonanonic | 101 | 93.5% | 93.5% | 0.3% free acid off white powder |
| Decanoic | 97 | 87% | 85.4% | no free acid off white powder |
| Undeca-noic | 101–104 | 98.9% | 100% | white powder trace of free acid |
| Dodeca-noic | 60–61* | 80% | 70% | 2% free acid off white powder |
| Octadeca-noic | 92 | 83% | 74% | no free acid white powder |
| Nonanonic and deca-noic in equimolar ratio | 90 | 86% | 90% | 1–4% free C$_9$ acid 1–3% free C$_{10}$ acid off white powder |

*Melting point reduced by methyldodecanoate impurity.

Example 2

Samples of esterified cellobiose prepared in accordance with Example 1 were used to gel various water-immiscible liquids and mixtures of liquids. The procedure was as follows:

0.5 grams esterified cellobiose and 9.5 grams of the liquid (or other proportions to give a total of 10 grams) were weighed directly into a 15 gram or 30 gram glass jar. A small magnetic follower was placed in the jar which was then placed on a hot plate. It was stirred and heated until all of the esterified cellobiose had dissolved in the liquid. This "dissolution temperature" was noted. The jar was then removed from the hot plate, the stirrer was removed from the hot liquid in the jar. A thermometer was placed in the liquid and the contents of the jar were then left undisturbed to cool. The gelling temperature, i.e. the temperature at which the contents gelled, was noted. The jar was left to stand for 24 hours and then the contents of the jar were inspected visually, pressed with a probe and classified qualitatively according to their appearance as a soft, medium or hard gel. The clarity or otherwise of the gel was noted. In most instances the gel was remelted, the remelting temperature was noted, and some of the melt was poured into a plastic (polymethylmethacrylate) cuvette and allowed to cool back to ambient laboratory temperature so that the gel reformed in the cuvette. The transmittance of light through the 1cm thickness of gel in the cuvette was determined at a wave length of 580 nm using an ultraviolet/visible spectrophotometer.

The following tables show the water-immiscible liquids which were used, the percentage of esterified cellobiose structurant used to gel the liquid, and some or all of the dissolution temperature, the gelling temperature, the visual appearance of the gel the remelt temperature and the percentage light transmittance (denoted as % T) through 1cm of the gel at 580 nm. In a few instances gel-formation was carried out as a test on a smaller scale, and less data could be recorded.

Gelling with α-cellobiose octa-hexanoate ("CB6" R = —$COC_5H_{11}$)

| Liquid | CB6 | Diss Temp | Gel Temp | Remelt Temp | % T | Visual appearance of gel |
|---|---|---|---|---|---|---|
| ISA (6) | 5 | 53 | 26 | 45 | 76 | Soft & transparent |
| DC 345 (2) | 5 | 90 | 59 | 70 | 0.03 | Medium & opaque |
| DC 556 (3) | 5 | 58 | 30 | 50 | 78 | V. soft & transparent |
| Silkflo 364 NF (5) | 5 | 80 | 65 | 70 | 27 | v. soft & transparent |
| Fluid AP (9) | 5 | 65 | 30 | 53 | 46 | Soft & transparent |
| DC 345: Fluid AP 80:20 wt ratio | 5 | 72 | 30 | 55 | 56 | Medium/hard & transparent |

Gelling with α-cellobiose octa-heptanoate ("CB7" R = —$COC_6H_{13}$)

| Liquid | CB6 | Diss Temp | Gel Temp | Remelt Temp | % T | Visual appearance of gel |
|---|---|---|---|---|---|---|
| ISA (6) | 5 | 41 | 25 | 41 | | Very soft & transparent —> crystal growth occurs |
| DC 345 (2) | 5 | 51 | 38 | 51 | | Medium & transparent —> crystal growth |
| Silkflo 364 NF (5) | 5 | 57 | 48 | 57 | | Very soft & opaque |
| Fluid AP (9) | 5 | 55 | 35 | 55 | | Very soft & opaque —> crystal growth |

Gelling with α-cellobiose octa-octanoate ("CB8" R = $COC_7H_{15}$)

| Liquid | CB6 | Diss Temp | Gel Temp | Remelt Temp | % T | Visual appearance of gel |
|---|---|---|---|---|---|---|
| ISA (6) | 5 | 41 | 30 | 41 | | Hard & transparent —> crystal growth |
| | 10 | 41 | 35 | | | Hard & translucent —> crystal growth |
| DC 345 (2) | 5 | 48 | 41 | 50 | 17 | Hard & transparent/translucent |
| | 10 | 53 | 50 | | | Hard & opaque |

Gelling with α-cellobiose octa-octanoate ("CB8" R = $COC_7H_{15}$) -continued

| Liquid | CB6 | Diss Temp | Gel Temp | Remelt Temp | % T | Visual appearance of gel |
|---|---|---|---|---|---|---|
| DC 556 (3) | 5 | 48 | 30 | 45 | 49 | Hard & transparent |
| | 10 | 49 | 35 | | | Hard & transparent |
| Silkflo 364 NF (5) | 5 | 53 | 45 | 51 | 22 | Hard & transparent |
| | 10 | 55 | 50 | | | Hard & opaque |

Gelling with α-cellobiose octa-nonanoate ("CB9" R = $COC_8H_{17}$)

| Liquid | CB6 | Diss Temp | Gel Temp | Remelt Temp | % T | Visual appearance of gel |
|---|---|---|---|---|---|---|
| ISA (6) | 5 | 57 | 25 | 46 | 78 | Medium/hard & transparent |
| DC 345 (2) | 5 | 62 | 42 | 60 | 15 | Hard & transparent/translucent |
| DC 566 (3) | 5 | 69 | 29 | 52 | 81 | Hard & transparent |
| Silkflo 364 NF (5) | 5 | 71 | 40 | 55 | 78 | Hard & transparent |
| Fluid AP (9) | 5 | 82 | 38 | 55 | 37 | Soft/medium & transparent |
| DC 345: Fluid AP 80:20 wt ratio | 5 | 68 | 28 | 54 | 39 | Soft/medium & transparent |
| DC 710 (4) | 5 | 82 | 48 | 62 | 11 | Medium & translucent |
| DC 710: DC 345 60:40 wt ratio | 5 | 74 | 33 | 60 | 4 | Hard & translucent |

Gelling with α-cellobiose octa-decanoate ("CB10" R = $COC_9H_{19}$)

| Liquid | CB6 | Diss Temp | Gel Temp | Remelt Temp | % T | Visual appearance of gel |
|---|---|---|---|---|---|---|
| Finsolv TN (7) | 5 | 72 | 25 | 38 | | Very soft & transparent gel |
| ISA (6) | 5 | 72 | 25 | 47 | 46 | Medium & transparent |
| | 7 | 68 | 25 | 52 | | Hard & translucent |
| | 10 | 76 | 30 | | | Medium & transparent |
| DC 345 (2) | 5 | 85 | 62 | 71 | 0.02 | Hard & translucent/opaque |
| | 7 | 84 | 65 | 59 | | Hard & opaque |
| DC 556 (3) | 3 | 79 | 46 | 59 | | Medium & transparent |
| | 5 | n/d | 50 | 52 | 2 | Medium/hard & translucent |
| | 7 | 74 | 40 | 67 | | Hard & translucent |
| Fluid AP (9) | 3 | 85 | 35 | 60 | | Medium & transparent |
| | 5 | 82 | 33 | 51 | | Medium & transparent |
| | 7 | 78 | 51 | 53 | 3 | Medium & translucent |
| | 10 | 84 | 45 | | | Medium & translucent/opaque |
| DC 345: Fluid AP 80: 20 wt ratio | 5 | 73 | 25 | 55 | <0.01 | Medium & translucent/opaque |
| | 7 | 82 | 36 | 49 | | Hard & opaque |
| | 10 | 83 | 41 | | | Hard & opaque |
| DC 710 (4) | 5 | 100 | 80 | 80 | 0.15 | Medium & opaque |
| DC 710: DC 345 60: 40 wt ratio | 5 | 92 | 65 | 65 | 1 | Medium & translucent/opaque |

| Gelling with α-cellobiose octa-undecanoate ("CB11" R = COC$_{10}$H$_{21}$) | | | |
|---|---|---|---|
| Liquid | % CB11 | % T | Visual appearance of gel |
| ISA (6) | 5 | — | Opaque gel |
| DC 245 (1) | 5 | 0.4 | Opaque gel |
|  | 5 | 34 | Transparent gel |
| DC 556 (3) | 10 | 22 | Transparent gel |
|  | 15 | 18 | Almost transparent gel |
|  | 5 | 58 | Transparent gel |
| Silkflo 364 NF (5) | 10 | 45 | Transparent gel |
|  | 15 | 37 | Transparent gel |
|  | 5 | — | Opaque soft gel |
| Mineral oil (8) | 10 | — | Opaque gel |
| Fluid AP (9) | 5 | — | Opaque gel |
| DC 245:Finsolv TN | 5 | 3 | Transparent gel |
| 80:20 wt ratio | 15 | 0.3 | Opaque gel |
| DC 245:Silkflo 364 NF | 5 | 5.2 | Translucent gel |
| 40:60 wt ratio | 10 | 1.0 | Translucent gel |
|  | 15 | 1.3 | Translucent gel |
| DC 245:Silkflo 364 NF | 5 | 28 | Transparent gel |
| 20:80 wt ratio | 10 | 21 | Transparent gel |
|  | 15 | 11 | Translucent gel |
| DC 710 (4):DC 245 | 5 | 13 | Almost transparent gel |
| 60:40 wt ratio | 10 | 7 | Translucent gel |

| Gelling with α-cellobiose octa-dodecanoate ("CB12" R = COC$_{11}$H$_{23}$) | | | | | |
|---|---|---|---|---|---|
| Liquid | % CB12 | Diss Temp | Gel Temp | Remelt Temp | % T | Visual appearance of gel |
| ISA (6) | 5 | 54 | 30 | 48 | 12 | Soft & transparent/translucent |
| DC 345 (2) | 5 | 50 | 48 | 50 | 0.17 | Soft & opaque |
| DC 556 (3) | 5 | 60 | 35 | 48 | 17 | Medium & transparent/translucent |
| Silkflo 364 NF (5) | 5 | 53 | 45 | 55 | 3 | Medium & transparent |
| Fluid AP (9) | 5 | 63 | 43 | 55 | 4 | Soft & transparent/translucent |
| DC 345: Finsolv TN 80:20 wt ratio | 5 | 65 | 29 | 42 | 3 | soft & translucent |
| DC 345: Fluid AP 80: 20 wt ratio | 5 | 63 | 42 | 50 | 0.25 | Soft/medium & opaque |
| DC 710 (4) | 5 | 65 | 57 | 65 | 1 | Medium & opaque |
| DC 710: DC 345 60:40 wt ratio | 5 | 65 | 48 | 55 | 39 | Soft & transparent |

| Gelling with α-cellobiose octa-octadecanoate ("CB18" R = COC$_{17}$H$_{35}$) | | | | | | |
|---|---|---|---|---|---|---|
| Liquid | % CB18 | Diss Temp | Gel Temp | Remelt Temp | % T | Visual appearance of gel |
| Finsolv TN (7) | 5 | 68 | 47 | 60 | 0.12 | very soft & opaque |
|  | 7 | 68 | 47 |  |  |  |
| IPM (10) | 5 | 68 | 50 | 59 | 0.01 | very soft & opaque |
|  | 7 | 72 | 50 |  |  | very soft & opaque |
| ISA (6) | 5 | 68 | 58 | 62 | 0.03 | very soft & opaque |
|  | 7 | 70 | 61 |  |  | soft & opaque |
| DC 345 (2) | 5 | 85 | 82 | 80 | <0.01 | soft & opaque |
|  | 7 | 87 | 86 |  |  | soft & opaque |
|  | 10 | 85 | 84 |  |  | medium & opaque |
| DC 556 (3) | 5 | 77 | 76 | 75 | 0.08 | soft & opaque |
|  | 7 | 83 | 79 |  |  | soft & opaque |
|  | 10 | 83 | 79 |  |  | medium & opaque |
| Silkflo 364 NF (5) | 5 | 72 | 66 | 75 | 0.11 | medium & opaque |
|  | 7 | 72 | 68 |  |  | medium & opaque |
|  | 10 | 79 | 69 |  |  | medium & opaque |
| Fluid AP (9) | 5 | 78 | 76 | 78 | 0.01 | soft & opaque |
|  | 7 | 82 | 77 |  |  | medium & opaque |
|  | 10 | 82 | 81 |  |  | soft & opaque |

Example 3

Cellobiose was esterified with a less than stoichiometric quantity of nonanoic acid to yield a partially esterified product, following a procedure generally similar to that of Example 1.

The following materials were used:

β-D-cellobiose, 2.5 grams, 7.3×10$^{-3}$ moles
Nonanoic acid, 5.78 grams, 3.65×10$^{-2}$ moles
Trifluoroacetic anhydride, 2.91 grams, 1.38×10$^{-2}$ moles.

Into a 3-neck round bottomed flask equipped with an overhead stirrer, water condenser and addition inlet was placed the nonanoic acid together with the trifluoroacetic anhydride. The resultant clear mixture was stirred and heated to 100° C. The colour of the reaction mixture darkened. The cellobiose was slowly added and a grey suspension was formed. The reaction mixture was kept at 100° C. for 6 hours then allowed to cool to ambient laboratory temperature. 100 ml of ice-cold methanol containing 10% water was mixed with the contents of the reaction flask. A fine white product was formed. This was filtered off and washed with further portions of methanol/water before drying in a vacuum oven. The yield was 2.5 grams.

The infra-red spectrum showed absorption peaks at 1744 and 3340 cm$^{-1}$ corresponding to the ester carbonyl group and free hydroxyl groups respectively. Mass spectrometer showed the presence of unacylated cellobiose and the penta-, hexa-, hepta- and octa-nonanoate esters of the cellobiose. The mono- di- and tri-esters could not be observed.

The ability of this partially esterified cellobiose to gel water-immiscible liquids was tested using the following procedure in which fully acylated cellobiose was included for comparison. In this procedure a large number of gels can be prepared simultaneously.

Gels were prepared in a 96 well (8 by 12 row) glass micro-titre plate. Each well had a volume of about 1 ml. About 0.01 g of each esterified cellobiose material was placed into 8 consecutive wells in a single row. Approximately 0.2 g of the required liquid was added to each well. A glass lid was placed on top of the plate. The plate was carefully placed in a thermostatically controlled fan assisted box oven at 150° C. for 2.5 hours. The plate was then removed from the oven and allowed to cool naturally to ambient laboratory temperature. The contents of each well were evaluated after 18 hours. Evaluation was carried out by visual inspection and by poking the contents of each well with a micro-spatula.

The results obtained were:

| Liquid | Fully acylated αC9 Cellobiose | Partially acylated αC9 Cellobiose | Fully acylated αC10 Cellobiose |
|---|---|---|---|
| Mineral oil (8) | hard gel | no gel | hard gel |
| Fluid AP (9) | medium hard gel | soft gel | hard gel |
| Polydecene (5) | hard gel | soft gel | hard gel |
| DC 556 (3) | hard gel | soft gel | hard gel |
| Isostearyl alcohol (6) | hard gel | no gel | hard gel |

This demonstrates that partially esterified cellobiose can be used, but the fully esterified compound is superior.

Example 4

Antiperspirant suspension sticks were prepared using a water-immiscible liquid or a mixture of water-immiscible liquids, an antiperspirant active and an esterified cellobiose. In all cases the procedure was as follows: the liquid or mixture of liquids was heated to a temperature 5 to 10° C. above a temperature at which the esterified cellobiose had been observed to dissolve in a preliminary test. During this heating the liquid was mixed gently using a Silverson mixer. The esterified cellobiose was added and allowed to dissolve. Next, the particulate antiperspirant active was added to this solution. The resulting mixture was then allowed to cool (or, if necessary, heated) whilst mixing gently until it reached a temperature of about 5 to 10° above the gelling point. At this stage the mixture was poured into antiperspirant stick barrels and left to cool without further disturbance until the formulation had solidified.

The resulting sticks were evaluated after at least 24 hours at ambient laboratory temperature. In all cases the appearance of the stick was noted, the hardness was determined by penetrometer and texture analyser, and tests of deposition and whiteness of the resulting deposit were carried out using the procedures described earlier.

The formulations which were prepared and the properties of the resulting sticks are set out in the table below. The testing of hardness and whiteness of deposit was also carried out with a commercial white solid stick (CWS) structured with 15% stearyl alcohol and 3% castor wax, these percentages being by weight of its whole composition.

"Esterified cellobiose $C_{12}$" denotes cellobiose esterified with dodecanoic acid, as in Example 1.

"Esterified cellobiose $C_9/C_{10}$" denotes cellobiose esterified with an equimolar mixture of nonanoic and decanoic acids, as in Example 1.

|  | CWS | 4.1 | 4.2 | 4.3 | 4.4 | 4.5 | 4.6 | 4.7 |
|---|---|---|---|---|---|---|---|---|
|  |  | % by Weight |  |  |  |  |  |  |
| Cyclomethicone, DC 245 (1) |  | 68.50 | 54.80 | 52.80 | 66.00 | 51.05 | 52.80 | 66.00 |
| Polydecene (5) |  | — | 13.70 | 13.20 | — | 9.95 | 13.20 | — |
| Esterified cellobiose $C_{12}$ |  | 7.50 | 7.50 | 10.00 | 10.00 | 15.00 | — | — |
| Esterified cellobiose $C_9/C_{10}$ |  | — | — | — | — | — | 10.00 | 10.00 |
| AZAG 7167 (12) |  | 24.00 | 24.00 | 24.00 | 24.00 | 24.00 | 24.00 | 24.00 |
| penetration depth (mm) | 9.40 | — | 11.2 | 13.5 | 12.6 | — | 16.2 | 12.0 |
| Hardness by texture analyser (N/mm²) | — | — | 0.26 | 0.18 | 0.21 | 0.50 | 0.11 | 0.24 |
| Whiteness on grey paper 24 hours after deposition | 118 | 80 | 26 | 25 | 50 | — | 25 | 37 |
| Whiteness on black wool 24 hours after deposition | 186 | 102 | 18.5 | 27 | 90 | — | 28 | 92 |

Example 5

Two soft solid products were prepared with the following formulations:

| Ingredient | % by weight |  |
|---|---|---|
| Cyclomethicone DC 245 (1) | 55.0 | 55.45 |
| Polydecene (5) | 13.0 | 13.86 |
| Esterified cellobiose (fully esterified with C18 fatty acid) | 4.0 | — |
| Esterified cellobiose (fully esterified with C9 and C10 fatty acids) | — | 2.97 |
| Talc (14) | 4.0 | 3.96 |
| AZAG 7.167 (12) | 24.0 | 23.76 |

The liquids and esterified cellobiose structurant were mixed together and heated with gentle stirring from a Silverson mixer to reach a temperature about 20–30° C. above the minimum temperature at which the esterified cellobiose would dissolve. The particulate antiperspirant active and talc were both added with more vigorous mixing. The mixture was then cooled further with continued mixing until the temperature had fallen to somewhat below a gelation temperature measured during a preliminary test. Then the mixture (which was still mobile) was poured into stick barrels and left to cool to ambient laboratory temperature.

Both formulations were spreadable and extrudable soft solids which was nevertheless capable of sustaining their own shape during storage for a period of 24 hours at 50° C.

Example 6

Opaque emulsion sticks were prepared with formulations as set out in tables below.

To prepare these sticks, the cyclomethicone was mixed with the other organic liquids (if any) including the cetyl dimethicone copolyol which functioned as an emulsifier (silicone surfactant) and the mixture was heated with gentle stirring to a temperature 5 to 10° C. above the temperature at which the structurant had been found to dissolve. The esterified cellobiose was then added and allowed to dissolve.

The disperse phase (also referred to as internal phase) was an aluminium zirconium active dissolved in water or in a mixture of a polyol and water. This disperse phase was pre-heated to the same temperature as the organic oils containing the esterified cellobiose and added slowly to them over a period of one minute while mixing with a Silverson mixer. After addition was complete the formulation was mixed at higher speed for five minutes. Stirring speed was then reduced for a further one minute after which the mixture was poured into stick barrels and allowed to cool undisturbed to ambient laboratory temperature. The sticks were tested by penetrometer, by texture analyser and for whiteness of deposits, in each instance by the test procedures given earlier. All of the sticks were opaque although without the chalky white appearance of a commercial white stick structured with stearyl alcohol and castor wax.

| Examples | 6.1 | 6.2 | 6.3 | 6.4 | 6.5 | 6.6 |
|---|---|---|---|---|---|---|
| | % by weight | | | | | |
| Cyclomethicone DC 245 (1) | 18 | 22.25 | 21.7 | 45.5 | — | — |
| Cyclomethicone DC 345 (2) | — | — | — | — | 23.8 | 24.4 |
| Mineral Oil (8) | — | — | — | — | 22.9 | 23.4 |
| Polydecene (5) | 22.75 | 27.5 | 27.4 | — | — | — |
| PPG-14 Butyl Ether (9) | 4.5 | 5.5 | 5.4 | — | — | — |
| Esterified cellobiose –$C_9$ | 3.75 | 3.75 | 4.5 | — | — | — |
| Esterified cellobiose –$C_{10}$ | — | — | — | 2.5 | 4.8 | 2.4 |
| Cetyl Dimethicone Copolyol (11) | 1 | 1 | 1 | 2 | 1 | 1 |
| Zirkonal 50 (13) | 40 | 40 | 40 | 40 | 38 | 38 |
| Glycerol (15) | — | — | — | — | 9.5 | 10.8 |
| Water | 10 | — | — | 10 | — | — |
| | Properties | | | | | |
| penetration depth (mm) | 16.8 | 17.5 | 15.7 | 40 | 12.5 | — |
| Hardness by texture analyser (N/mm$^2$) | 0.11 | 0.10 | 0.12 | — | — | — |
| Whiteness on grey paper 24 hours after deposition | 19 | 16 | 16 | 31 | — | — |
| Whiteness on black wool 24 hours after deposition | 28 | 29 | 27 | 11 | — | — |

N.B. 40% of Zirkonal 50 provides 20% of antiperspirant active and 20% of water.

| | Examples | | | | | |
|---|---|---|---|---|---|---|
| | 6.7 | 6.8 | 6.9 | 6.10 | 6.11 | 6.12 |
| | % by weight | | | | | |
| Cyclomethicone DC 245 (1) | — | 23.5 | 20.95 | 19.8 | 20.95 | 22.3 |
| Cyclomethicone DC 345 (2) | 23.3 | — | — | — | — | — |
| Mineral Oil (8) | 23.3 | 22.2 | — | — | — | 21.0 |
| Polydecene (5) | — | — | — | 25.9 | — | — |
| PPG-14 Butyl Ether (9) | — | — | — | — | — | — |
| DC 556 (3) | — | — | 24.75 | — | — | — |
| Isostearyl alcohol (6) | — | — | — | — | 24.8 | — |
| Esterified cellobiose-$C_9$ | — | — | — | — | — | — |
| Esterified cellobiose-$C_{10}$ | 2.4 | 2.5 | 2.5 | 2.5 | 2.5 | 5 |
| Cetyl Dimethicone Copolyol (11) | 1 | 1.8 | 1.8 | 1.8 | 1.75 | 1.7 |
| Zirkonal 50 (13) | 40 | 40 | 40 | 40 | 40 | 40 |
| Glycerol (15) | 10 | 10 | 10 | 10 | 10 | 10 |
| Water | — | — | — | — | — | — |
| | Properties | | | | | |
| penetration depth (mm) | | 22.7 | 25.6 | 25.0 | 29.0 | 17.8 |
| Hardness by texture analyser (N/mm$^2$) | | — | | | | |
| Whiteness on grey paper 24 hours after deposition | | 27 | 25 | 22 | 23 | 28 |
| Whiteness on black wool 24 hours after deposition | | 17 | 13 | 15 | 11 | 16 |

Example 7

A number of oils, with various values of refractive index, were gelled with cellobiose octa-ester, or with another structurant as stated in the table below. The clarity of the gels was assessed by measuring light transmission at 580 nm, when a 1cm thickness of gel in a cuvette was placed in a spectrophotometer light beam at 20–25° C.

Results are given in the following table, where Refractive index mismatch=Refractive index of liquid–Refractive index of structurant.

| Structurant and its Refractive index | Refractive index mismatch | | | | |
|---|---|---|---|---|---|
| | −0.08 | −0.04 | −0.02 | 0.0 | +0.06 |
| 5% cellobiose octa-nonanoate (~1.48) | 16% | 40% | 63% | ~100% | 13% |
| 5% cellobiose octa-dodecanoate (~1.48) | <0.2% | 2% | 16% | 40% | 3% |
| 5% cellobiose octa-octadecanoate (~1.48) | <0.01% | <0.01% | <0.1% | 6% | <0.05% |
| 4% N-lauroyl glutamic acid di-n-butylamide (GP1) (~1.48) | <0.01% | <0.01% | 6% | 63% | 25% |
| 2.5% 12-hydroxy stearic acid (~1.52) | 16% | 40% | 63% | ~100% | no data |

It can be seen that mis-match of refractive index reduces light transmittance. Cellobiose octa-nonanoate is much more tolerant of mismatch than are esters of cellobiose with longer acids and the N-acylaminoacid amide gellants. 12-hydroxy stearic acid is also tolerant of mis-match but requires the liquids to be matched to its higher refractive index.

Example 8

The procedure of Example 6 was repeated to prepare a number of emulsion sticks with formulations set out in the following tables. The continuous and disperse phases were formulated to have refractive indices which matched closely at the value given in the tables. These sticks were tested as before and the properties are also given in these tables.

|  | Examples | | | | | |
| --- | --- | --- | --- | --- | --- | --- |
|  | 8.1 | 8.2 | 8.3 | 8.4 | 8.5 | 8.6 |
|  | % by weight | | | | | |
| Cyclomethicone DC245 (1) | 22.625 | 18.75 | 25.5 | 19 | 26 | 17.75 |
| Mineral Oil (8) | 22.625 | — | — | — | — | — |
| Polydecene (5) | — | 22.5 | 15.75 | 22 | 15 | 22 |
| PPG-14 Butyl Ether (9) | — | 4 | 4 | — | — | 4.25 |
| Isostearyl Alcohol (6) | — | — | — | 4.25 | 4.25 | — |
| Esterified Cellobiose $C_9$ | 3.75 | 3.75 | 3.75 | 3.75 | 3.75 | 5 |
| Cetyl Dimethicone Copolyol (11) | 1 | 1 | 1 | 1 | 1 | 1 |
| Zirkonal 50 (13) | 40 | 40 | 40 | 40 | 40 | 40 |
| Glycerol (15) | 10 | 10 | 7.5 | 10 | 7.5 | 10 |
| Water | — | — | 2.5 | — | 2.5 | — |
| PG (16) | — | — | — | — | — | — |
| AZG 375 (18) | — | — | — | — | — | — |
|  | Properties | | | | | |
| Matched Refractive index of phases | 1.43 | 1.43 | 1.425 | 1.435 | 1.425 | 1.43 |
| penetration depth (mm) | 19.3 | 18.5 | 17.3 | 24.7 | 23.6 | 12.4 |
| Hardness by texture analyser (N/mm$^2$) | 0.11 | 0.12 | 0.08 | 0.07 | 0.06 | 0.17 |
| Whiteness on grey paper 24 hours after deposition | — | 15 | 16 | 18 | 19 | 16 |
| Whiteness on black wool 24 hours after deposition | — | 24 | 28 | 25 | 30 | 26 |
| Transmittance at 580 nm | — | 38% | 33% | 41% | 35% | 51% |

|  | Examples | | | | | |
| --- | --- | --- | --- | --- | --- | --- |
|  | 8.7 | 8.8 | 8.9 | 8.10 | 8.11 | 8.12 |
|  | % by weight | | | | | |
| Cyclomethicone DC245 (1) | 16.75 | 18 | | 14.02 | 28.4 | 4.5 |
| Cyclomethicone DC345 (2) | | | | | | 4.4 |
| Mineral Oil (8) | | | | | | 43.4 |
| Polydecene (5) | 20.75 | 22.75 | 17.72 | 13.1 | 50.75 | |
| PPG-14 Butyl Ether (9) | 4 | 4.5 | 3.51 | 3.75 | — | |
| Isostearyl Alcohol (6) | — | — | — | — | — | |
| Esterified Cellobiose $C_9$ | 7.5 | 3.75 | 3.75 | 3.75 | 3.75 | |
| Esterified Cellobiose $C_{10}$ | | | | | | 2.4 |
| Cetyl Dimethicone Copolyol (11) | 1 | 1 | 1 | 1 | 1 | 1 |
| Zirkonal 50 (13) | 40 | — | 40 | 40 | — | |
| Westwood Active (17) | | | | | | 48.8 |
| Glycerol (15) | 10 | 4 | 17.5 | 6.25 | 12 | |
| Water | — | 14 | 2.5 | 3.75 | 8 | |
| PG (16) | — | 12 | — | — | — | |
| AZG 375 (18) | — | 20 | — | — | 20 | |
|  | Properties | | | | | |
| Matched Refractive index of phases | 1.43 | 1.43 | 1.43 | 1.42 | 1.45 | 1.46 |
| penetration depth (mm) | 11 | 14.5 | 14.9 | 15.1 | 14.8 | — |
| Hardness by texture analyser (N/mm$^2$) | 0.29 | 0.11 | 0.14 | 0.13 | 0.11 | — |
| Whiteness on grey paper 24 hours after deposition | 17 | 20 | 18 | 21 | 16 | — |
| Whiteness on black wool 24 hours after deposition | 25 | 28 | 25 | 31 | 19 | — |
| Transmittance at 580 nm | 48% | 82% | 65% | 30% | 72% | 74% |

| Examples | 8.13 | 8.14 | 8.15 | 8.16 | 8.17 |
| --- | --- | --- | --- | --- | --- |
|  | % by weight | | | | |
| Cyclomethicone DC245 (1) | 41.85 | 35.4 | 10.04 | 10.64 | 6.96 |
| Permethyl 101A (19) | 2.15 | | | | |
| Permethyl 102A (20) | — | 8.6 | | | |
| Polydecene (5) | | | 12.7 | 13.45 | 8.8 |
| PPG-14 Butyl Ether (9) | | | 2.51 | 2.66 | 1.74 |
| Esterified Cellobiose $C_9$ | 5 | 5 | 3.75 | 2.25 | 1.5 |
| Cetyl Dimethicone Copolyol (11) | 1 | 1 | 1 | 1 | 1 |
| Zirkonal 50 (13) | 40 | 40 | 52.71 | 52.71 | 60.24 |
| Glycerol (15) | 0.75 | 4.5 | 17.29 | 17.29 | 19.76 |
| Water | 9.25 | 5.5 | — | — | — |
|  | Properties | | | | |
| Matched refractive index of phases | 1.40 | 1.41 | 1.43 | 1.43 | |
| penetration depth (mm) | 13.5 | 13.2 | 12.0 | 16.8 | |
| Hardness by texture analyser (N/mm$^2$) | 0.16 | 0.15 | 0.13 | 0.07 | |
| Whiteness on grey paper 24 hours after deposition | 59 | 61 | 24 | 24 | |
| Whiteness on black wool 24 hours after deposition | 122 | 24 | 15 | 16 | |
| Transmittance at 580 nm | 2.7% | 5% | 33% | 73% | |

In the above table Example 8.17 is a stick with a high percentage of internal phase. It was observed to have good clarity, but was not very hard (although capable of sustaining its own shape).

Example 9

α-cellobiose octanoate was deacylated at the anomeric carbon atom by reaction with a mixture of acetic acid and ethylene diamine, in an adaptation of a procedure given at J.Carb.Chem 18 pages 461–469 (1999).

The procedure was as follows:
Glacial acetic acid (0.6 g) was added slowly dropwise with stirring to a solution of ethylene diamine (1.2 G) in THF (250 cm$^3$). A white precipitate formed which remained during the reaction. Cellobiose Octanonanoate (14.6 g) was then added and the whole reaction mixture stirred at room temperature for a total of 48 hours. After this time the contents of the flask were transferred to a one litre separating funnel, 100 cm$^3$ of water was then added and the mixture extracted with dichloromethane (250 cm$^3$). The organic layer was collected and further washed with 100 cm$^3$ portions of dilute HCl (0.1M), aqueous sodium bicarbonate (1M) and water. The resultant organic phase was then dried over anhydrous magnesium sulphate, filtered and the remaining solvent removed by rotary evaporation. A slightly sticky off-white crude solid was obtained, this was dissolved in THF (20 cm$^3$) in a 500 cm$^3$ conical flask, heated on a steam bath then methanol (about 150 cm$^3$) added slowly, the resultant solution was kept on the steam bath for 3–4 minutes then removed and allowed to cool down to room temperature overnight. Next morning the white solid precipitate was filtered off, dried and collected.

The product was obtained in a quantity of 6.8 g (51% yield). It had a melting point of 100° C. and purity determined by high performance liquid chromatography was 98.5%.

Its structure was checked by mass spectrometer (molecular ion of mass 1341) proton n.m.r. and infra red (peaks at 3446, 2923, 2853 and 1742 cm$^{-1}$). The material was found to be the β-anomer of cellobiose heptanonanoate. The reaction can thus be represented as:

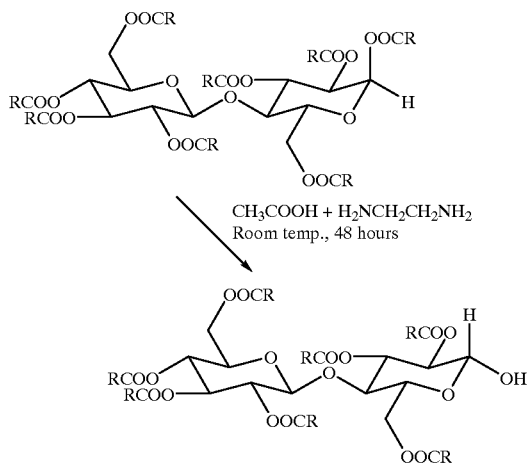

The material was used to gel some water-immiscible liquids as in Example 2. The results are given in the following table.

Gelling with β-cellobiose hepta-nonanoate "CB-HN"

| Liquid | % CB | Diss Temp | Gel Temp | Visual appearance of gel |
|---|---|---|---|---|
| DC 345 (2) | 5 | 82 | 67 | Opaque gel |
| DC 556 (3) | 5 | — | — | Opaque gel |
| Silkflo 364NF (5) | 10 | — | — | Very soft opaque gel |
| DC 345:Silkflo 364NF 80:20 wt ratio | 5 | 76 | 71 | Opaque soft gel |
| DC 345:Silkflo 364NF 50:50 wt ratio | 5 | 73 | 69 | Opaque soft gel |

Example 10

Sticks were prepared and tested in accordance with the procedure given in Example 6. The sticks were tested for hardness by texture analyser and/or by penetrometer. They were observed to give deposits of low whiteness, but numerical data were not recorded.

For some sticks in this example the refractive indices of the water-immiscible continuous phase and the polar antiperspirant active solution were matched sufficiently to give translucent sticks. Some values of transmittance are shown.

| Examples | 10.1 | 10.2 | 10.3 | 10.4 | 10.5 |
|---|---|---|---|---|---|
| | % by weight | | | | |
| DC245 (1) | 44 | 21.625 | 21.625 | 21.625 | 18 |
| Silkflo364 (5) | — | — | — | 21.625 | 4 |
| Permethyl 102A (20) | — | 21.625 | — | — | — |
| SF1555 (21) | — | — | 21.625 | — | 22 |
| Abil EM90 (11) | 1 | — | — | — | 1 |
| Quest PGPR (22) | — | 1.75 | 1.75 | 1.75 | — |
| Esterified Cellobiose -C9 | 5 | 5 | 5 | 5 | 5 |
| Zirkonal 50 (13) | 39 | 40 | 40 | 40 | 40 |
| Glycerol (15) | — | 8 | 9 | 8.75 | 10 |
| Water | 11 | 2 | 1 | 1.25 | — |
| | Properties | | | | |
| Penetration depth (mm) | 9.3 | 12 | 11.3 | 13 | |
| Hardness by texture analyser (N/mm$^2$) | 0.10 | 0.12 | 0.12 | 0.21 | 0.13 |

| Examples | 10.6 | 10.7 | 10.8 | 10.9 | 10.10 |
|---|---|---|---|---|---|
| | % by weight | | | | |
| Cyclomethicone DC 245 (1) | 7.6 | 6.8 | 36.5 | 1.7 | 1.25 |
| isostearyl alcohol (6) | — | — | — | 23.3 | — |
| octyldodecanol (23) | — | — | — | — | 23.1 |
| SF1555 (21) | 37.43 | 37.7 | 7 | — | — |
| Silkflo 364 (5) | — | — | — | 16.8 | 17.65 |
| Esterified Cellobiose -C10 | 8.12 | 7.3 | 7.8 | 7 | 7 |
| Cetyl Dimethicone Copolyol (Abil EM90) (11) | 1.1 | 1 | 1 | 1 | 1 |
| Westwood active (17) | 43.54 | 41 | 42 | 40 | 40 |
| Glycerol (15) | — | 4.7 | 5.2 | 6.8 | 6.5 |
| Water | 2.21 | 1.5 | 0.5 | 3.4 | 3.5 |
| | Properties | | | | |
| Matched RI of phases | 1.45 | 1.45 | 1.46 | 1.45 | 1.45 |
| penetration depth (mm) | 9.1 | 6.9 | 8.7 | 8.8 | 9.1 |
| Hardness by texture analyser (N/mm$^2$) | 0.37 | 0.03 | 0.08 | 0.04 | 0.19 |
| Transmittance at 580 nm (%) | 8 | 3 | 5 | 6 | 5 |

| Examples | 10.11 | 10.12 | 10.13 | 10.14 |
|---|---|---|---|---|
| | % by weight | | | |
| DC245 (1) | 12 | 11.32 | — | — |
| Silkflo 364 (5) | 32.5 | 30.68 | 39 | 41.5 |
| Abil EM90 (11) | 0.5 | 0.5 | 1 | 1 |
| Esterified Cellobiose -C10 | 5 | 7.5 | 10 | 7.5 |
| Zirkonal 50 (13) | 33 | 33 | — | — |
| Westwood active (17) | — | — | 48.06 | 48.06 |
| Glycerol (15) | 17 | 17 | — | — |
| water | — | — | 1.94 | 1.94 |
| | Properties | | | |
| penetration depth (mm) | 19 | 14 | 7.3 | 9.6 |
| Hardness by texture analyser (N/mm$^2$) | 0.44 | 0.07 | 0.47 | 0.15 |

Example 11

The procedure of Example 6 was repeated to prepare a number of emulsion sticks with formulations set out in the following tables. As in Example 8, the continuous and disperse phases were formulated to have refractive indices which matched closely at the value given in the tables. The sticks were tested for hardness by texture analyser and/or by penetrometer. They were observed to give deposits of low whiteness, consistent with their good clarity, but numerical data were not recorded.

The refractive indices of sample quantities of the water-immiscible liquid mixture and the antiperspirant active solutions were checked before making the sticks. If necessary their formulations were modified very slightly to optimise the refractive index match.

|  | Examples | | | | | |
|---|---|---|---|---|---|---|
|  | 11.1 | 11.2 | 11.3 | 11.4 | 11.5 | 11.6 |
|  | % by weight | | | | | |
| Permethyl 102A (20) | 41.36 | — | — | — | — | — |
| Panalene L-14E (24) | — | — | 22 | — | — | — |
| Fancol 800 (25) | — | — | — | 22 | 22 | — |
| Puresyn 4 (28) | — | — | — | — | — | 22 |
| DC245 (1) | 2.64 | 11.4 | 22 | 22 | 22 | 22 |
| SF 1555 (21) | — | 34.1 | — | — | — | — |
| Esterified cellobiose C9 | 5 | 4.9 | 5 | 5 | 5 | 5 |
| Abil EM90 (11) | 1 | 1 | 1 | 1 | 1 | 1 |
| Zirkonal 50 (13) | — | — | 40 | 40 | 36.6 | 40 |
| Westwood active (17) | 50 | 48.6 | — | — | — | — |
| Glycerol (15) | — | — | 9.35 | 7.5 | 13.4 | 8.75 |
| Water | — | — | 0.65 | 2.5 | — | 1.25 |
|  | Properties | | | | | |
| Matched refractive index of phases (at 25° C.) | 1.46 | 1.45 | 1.431 | 1.425 | 1.437 | 1.429 |
| penetration depth (mm) | 9 | 11 | 10.5 | 12.1 | 7.9 | 8.8 |
| Hardness by texture analyser (N/mm$^2$) | 0.11 | 0.11 | 0.13 | 0.12 | 0.11 | 0.10 |
| Transmittance at 580 nm (%) | 68 | 70 | 40 | 6 | 70 | 37 |

|  | Examples | | | | |
|---|---|---|---|---|---|
|  | 11.7 | 11.8 | 11.9 | 11.10 | 11.11 |
|  | % by weight | | | | |
| DC245 (1) | 22 | 22.25 | 22.25 | 21.625 | — |
| DC556 (3) | 22 | — | — | — | — |
| Silkflo 364 (5) | — | — | — | — | 44 |
| Permethyl 102A (20) | — | 22.25 | — | — | — |
| Panalene-L-14E (24) | — | — | — | 21.625 | — |
| SF1555 (21) | — | — | 22.25 | — | — |
| Abil EM90 (11) | 1 | 0.5 | 0.5 | — | 1 |
| Lameform TGI (26) | — | — | — | 0.875 | — |
| Dehymuls PGPH (27) | — | — | — | 0.875 | — |
| Esterified cellobiose C9 | 5 | 5 | 5 | 5 | 5 |
| Zirkonal 50 (13) | 40 | 40 | 40 | 40 | 50 |
| Glycerol (15) | 9 | 8 | 9 | 9.8 | — |
| Water | 1 | 2 | 1 | 0.2 | — |
|  | Properties | | | | |
| Matched refractive index of phases (at 25° C.) | 1.428 | 1.43 | 1.43 | 1.43 | 1.46 |
| penetration depth (mm) | 9.0 | 11 | 11 | 10.5 | 9 |
| Hardness by texture analyser (N/mm$^2$) | 0.10 | 0.09 | 0.16 | 0.13 | 0.13 |
| Transmittance at 580 nm (%) | 40 | 22 | 33 | 36 | 24 |

|  | Examples | | | | | |
|---|---|---|---|---|---|---|
|  | 11.12 | 11.13 | 11.14 | 11.15 | 11.16 | 11.17 |
|  | % by weight | | | | | |
| DC245 (1) | — | — | — | 22 | 22 | 18 |
| Silkflo 364 (5) | 44 | — | — | — | — | 5.3 |
| Permethyl 102A (20) | — | 44 | — | 22 | — | — |
| Panalene-L-14E (24) | — | — | 44 | — | — | — |
| SF 1555 (21) | — | — | — | — | 22 | — |
| Octyldodecanol (23) | — | — | — | — | — | 21.9 |
| Abil EM90 (11) | 1 | 1 | 1 | 1 | 1 | 1 |
| Esterified Cellobiose C9 | 5 | 5 | 5 | 5 | 5 | 5 |
| Zirkonal 50 (13) | 18 | 21.5 | 12 | — | — | 37.8 |
| AZG-375 (18) | — | — | — | 25 | 25 | — |
| Glycerol (15) | 32 | 28.5 | 38 | 0.6 | 2.5 | 11 |
| Water | — | — | — | 24.4 | 22.5 | — |
|  | Properties | | | | | |
| Matched refractive index of phases (at 25° C.) | 1.45 | 1.45 | 1.46 | 1.43 | 1.43 | 1.43 |
| penetration depth (mm) | 9 | 9 | 7 | 9 | 8 | — |
| Hardness by texture analyser (N/mm$^2$) | 0.13 | 0.15 | 0.20 | — | 0.21 | 0.12 |
| Transmittance at 580 nm (%) | 74 | 46 | 82 | 53 | 41 | 24 |

Example 12

The procedure of Example 6 was used to prepare a number of emulsion sticks with formulations set out in the following table. These sticks did not contain antiperspirant active. They would be useful as moisturizing stick or lip salve and their compositions could be used as the basis for other, probably opaque, cosmetic stick products. The continuous and disperse phases were formulated to have refractive indices which matched closely at the values given in the table, but evaporative losses during processing interfered with this. The sticks were tested for hardness by texture analyser and/or by penetrometer.

|  | Examples | | | |
|---|---|---|---|---|
|  | 12.1 | 12.2 | 12.3 | 12.4 |
|  | % by weight | | | |
| DC45 (1) | 22 | 22 | 16.72 | 19.36 |
| Silkflo 364 (5) | 22 | — | 27.28 | — |
| SF 1555 (21) | — | 22 | — | 24.64 |
| Abil EM90 (11) | 1 | 1 | 1 | 1 |
| Esterified Cellobiose C9 | 5 | 5 | 5 | 5 |
| Glycerol (15) | 33.5 | 37.5 | — | — |
| Water | 16.5 | 12.5 | — | — |
| Propylene Glycol (16) | — | — | 50 | 50 |
|  | Properties | | | |
| Matched refractive index of phases (at 25° C.) | 1.42 | 1.43 | 1.43 | 1.43 |
| penetration depth (mm) | 9 | 9 | — | 10 |
| Hardness by texture analyser (N/mm$^2$) | 0.13 | 0.15 | 0.15 | — |

Example 13

The procedure of Example 6 was used to prepare translucent emulsion sticks with the formulation below in which the structurant is α-cellobiose octa-undecanoate ("CB11"). As in Example 8, the continuous and disperse phases were formulated to have refractive indices which matched closely at the value given. The sticks were tested for hardness by texture analyser and/or by penetrometer. They were observed to give deposits of low whiteness.

| Ingredients | percent by weight |
|---|---|
| DC245 (1) | 11 |
| Silkflo 364 (5) | 33 |
| Abil EM90 (11) | 1 |
| Esterified Cellobiose C11 | 5 |
| Zirkonal 50 (13) | 33 |
| Glycerol (15) | 17 |
| Properties | |
| Matched refractive index of phases (at 25° C.) | 1.44 |
| penetration depth (mm) | 16 |
| Hardness by texture analyser (N/mm$^2$) | 0.05 |
| Transmittance at 580 nm (%) | 6 |

Example 14

The procedure of Example 6 was used to prepare an opaque emulsion stick of the following formulation, which included agents to assist wash-off.

| Ingredients | percent by weight |
|---|---|
| DC245 (1) | 16.4 |
| Silkflo 364 (5) | 24.6 |
| Abil EM90 (11) | 1 |
| Esterified cellobiose C9 | 5 |
| Zirkonal 50 (13) | 40 |
| Glycerol (15) | 10 |
| Ceteareth 20 (29) | 2.5 |
| C$_{20-40}$ alcohols (30) | 0.5 |

What is claim is:
1. A composition of matter suitable for cosmetic use comprising a continuous phase which contains a water-immiscible liquid carrier and a structurant therein which is at least partially esterified cellobiose of the formula

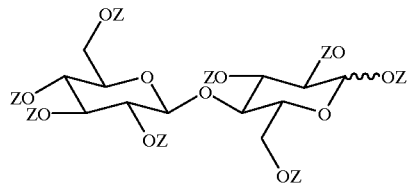

wherein each Z is independently hydrogen or an acyl group of the formula

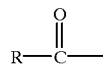

where R denotes a hydrocarbyl group containing from 4 to 22 carbon atoms, with the proviso that not more than half of the Z groups are hydrogen.

2. A composition according to claim 1 wherein at least five of every eight groups Z are said acyl groups.

3. A composition according to claim 1 wherein at least three-quarters of the said groups Z are said acyl groups.

4. A composition according to claim 2 wherein R denotes an akyl or alkenyl group of 5 to 18 carbon atoms.

5. A composition according to claim 2 wherein R denotes a linear alkyl group of 17 carbon atoms.

6. A composition according to claim 2 wherein R denotes an alkyl group of 5 to 12 carbon atoms.

7. A composition according to claim 2 wherein R denotes a linear alkyl group of 7 to 9 carbon atoms.

8. A composition according to claim 2 wherein R denotes a linear alkyl group of 10 carbon atoms.

9. A composition according to claim 2 wherein substantially all of the said groups Z are said acyl groups wherein R is linear alkyl of 7 to 9 carbon atoms.

10. A composition according to claim 2 wherein substantially all of the said groups Z are said acyl groups wherein R is linear alkyl of 10 carbon atoms.

11. A composition according to claim 1 characterised in that the water-immiscible liquid carrier contains a volatile silicone and optionally a non-volatile silicone and/or a non-silicone hydrophobic organic liquid selected from hydrocarbons, hydrophobic aliphatic esters, aromatic esters, hydrophobic alcohols and hydrophobic ethers.

12. A composition according to claim 1 wherein the water-immiscible carrier liquid contains silicone oil in an amount which is at least 10% by weight of the composition.

13. A composition according to claim 1 containing from 0.1 to 15% by weight of the structurant.

14. A composition according to claim 1 which contains not more than 5% by weight of any fatty alcohol which is solid at 20° C.

15. A composition according to claim 1 wherein the composition is an emulsion with a hydrophilic, water-miscible, disperse phase in addition to said water-immiscible liquid continuous phase.

16. A composition according to claim 15 wherein the disperse phase contains a diol or polyol.

17. A composition according to claim 15 which contains from 0.1% to 10% by weight of a nonionic emulsifier.

18. A composition according to claim 1 which does not contain more than 8% by weight of ethanol or any monohydric alcohol with a vapour pressure above 1.3 kPa at 22° C.

19. A composition according to claim 1 wherein the composition is a suspension with a particulate solid material dispersed in said liquid continuous phase.

20. A composition according to claim 1 which is a deodorant or antiperspirant composition comprising a deodorant or antiperspirant active.

21. A composition according to claim 1 which is an antiperspirant composition comprising a particulate antiperspirant active in suspension in said water-immiscible continuous phase.

22. A composition according to claim 1 which is an antiperspirant composition comprising an antiperspirant active dissolved in said disperse phase.

23. A composition according to claim 1 wherein the antiperspirant active comprises an aluminium and/or zirconium halohydrate, an activated aluminium and/or zirconium halohydrate, or an aluminium and/or zirconium complex or an activated aluminium and/or zirconium complex.

24. A composition according to claim 23 which is a halohydrate or complex in which aluminium and zirconium are both present.

25. A composition according to claim 1 wherein the proportion of antiperspirant active is from 5 to 40% by weight of the composition.

26. A composition according to claim 1 which is a firm gel such that a penetrometer needle with a cone angle of 9 degrees 10 minutes, drops into the gel for no more than 30 mm when allowed to drop under a total weight of 50 grams for 5 seconds.

27. A composition according to claim 1 which is translucent or transparent.

28. A composition according to claim 27 which has at least 1%, light transmittance at 580 nm through a 1cm thickness of the composition at 22° C.

29. An antiperspirant product comprising a dispensing container having at least one aperture for delivery of the contents of the container, means for urging the contents of the container to the said aperture or apertures, and a composition according to claim 1 accommodated within the container.

30. A product according to claim 29 wherein the composition is in the form of a stick and the container has an open end at which an end portion of the stick of composition is exposed for use.

31. A process for the production of a composition according to claim 1 comprising, not necessarily in any order, the steps of incorporating into a water-immiscible liquid carrier a structurant which is said wholly esterified or partially esterified cellobiose, if required, mixing the liquid carrier with a solid or a disperse liquid phase to be suspended therein, heating to an elevated temperature at which the structurant is in solution in the water-immiscible liquid carrier, followed by cooling or permitting the mixture to cool to a 58 temperature at which it is thickened or solidified.

32. A process according to claim 31 which includes a step of pouring the mixture at elevated temperature into a dispensing container and allowing it to cool therein so as to produce a product according to claim 29.

33. A method for preventing or reducing perspiration on human skin comprising topically applying to the skin a composition according to claim 1.

34. A composition according to claim 28 which has at least 3% light transmittance at 580 nm through a 1 cm thickness of the composition at 22° C.

* * * * *